United States Patent [19]

Pfammatter

[11] Patent Number: 5,606,100
[45] Date of Patent: Feb. 25, 1997

[54] PROCESS FOR THE PREPARATION OF TRIALKYL ESTER DERIVATIVES

[75] Inventor: Elmar Pfammatter, Visp, Switzerland

[73] Assignee: Lonza Ltd., Gampel/Valais, Switzerland

[21] Appl. No.: 571,652

[22] Filed: Dec. 13, 1995

[30] Foreign Application Priority Data

Dec. 21, 1994 [CH] Switzerland .............................. 3868/94

[51] Int. Cl.$^6$ ..................................................... C07C 69/34
[52] U.S. Cl. .............................................. 560/192; 558/52
[58] Field of Search ................................ 560/192; 558/52

[56] References Cited

FOREIGN PATENT DOCUMENTS 0369583  5/1990  European Pat. Off. .

OTHER PUBLICATIONS

H. Padgett et al., Jr. Org. Chem., vol. 44, No. 20, (1979), pp. 3492 to 3496.

H. Lund & A. Voigt in Organic Syntheses, Collect. vol. II, Wiley, New York (1946), p. 594.

*Primary Examiner*—Gary Geist
*Assistant Examiner*—Barbara S. Frazier
*Attorney, Agent, or Firm*—Fisher, Christen & Sabol

[57] ABSTRACT

A process for the preparation of trialkyl ester derivatives of the general formula:

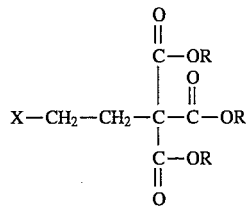

wherein X is chlorine, bromine, iodine, tosyloxy or mesyloxy and R is a $C_1$–$C_6$-alkyl group. According to this process, a trialkyl methanetricarboxylate of the general formula:

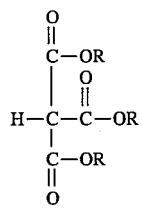

wherein R has the meaning given above, is converted to the end product of formula I with a disubstituted ethane of the general formula:

$$X-CH_2-CH_2-X \qquad \text{III}$$

wherein the two substituents X are identical or different and have the meaning given above, in the presence of an alkaline earth metal carbonate or alkali metal carbonate.

13 Claims, No Drawings

PROCESS FOR THE PREPARATION OF TRIALKYL ESTER DERIVATIVES

BACKGROUND OF THE INVENTION

1. Field Of The Invention

The invention relates to a novel process for the preparation of trialkyl ester derivatives of the general formula:

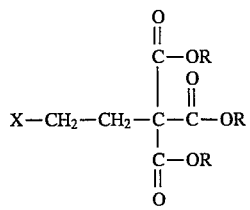

wherein X is chlorine, bromine, iodine, tosyloxy- or mesyloxy- and R is a $C_1$–$C_6$-alkyl group.

2. Background Art

Trialkyl ester derivatives of the formula I, for example, bromo triethyl esters, are valuable intermediates in the preparation of antiviral nucleotide derivatives (European Published Patent Application 0369583).

The preparation of bromo triethyl ester starting from triethyl methanetricarboxylate and dibromoethane in the presence of sodium ethanolate is known [H. Rapoport et al., J. Org. Chem., Vol. 44, No. 20, (1979), 3492–3496]. However, this prior process has, on the one hand, the disadvantage that the corresponding product is heavily contaminated with by-products and the fact, on the other hand, that it is uneconomic owing to relatively long reaction times involved.

BROAD DESCRIPTION OF THE INVENTION

The object of invention is to provide a more economic process for the preparation of trialkyl ester derivatives, in which the corresponding products are obtained in high purity. This object is achieved with the novel process of the invention.

The invention involves a process for the preparation of trialkyl ester derivatives of the general formula:

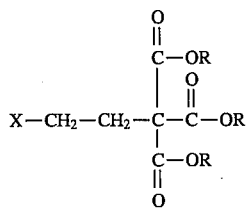

wherein X is chlorine, bromine, iodine, tosyloxy- or mesyloxy- and R is a $C_1$–$C_6$-alkyl group. In the process, a trialkyl methanetricarboxylate of the general formula:

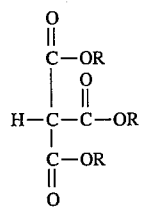

wherein R has the meaning given above, is converted into the end product of formula I with a disubstituted ethane of the general formula:

$$X\text{—}CH_2\text{—}CH_2\text{—}X \qquad III$$

wherein the two substituents X are identical or different and have the meaning given above, in the presence of an alkaline earth metal carbonate or an alkali metal carbonate.

Preferably the reaction is carried out in a polar aprotic solvent. Preferably dimethylformamide is employed as the polar aprotic solvent. Preferably the reaction is carried out in the presence of an alkali metal carbonate. Preferably the alkali metal carbonate employed is potassium carbonate or sodium carbonate. Preferably 1,2-dibromoethane is employed as the disubstituted ethane. Preferably the trialkyl methanetricarboxylate employed is triethyl methanetricarboxylate. Preferably the reaction is carried out at a temperature from 0° C. to the reflux temperature of the solvent concerned.

DETAILED DESCRIPTION OF THE INVENTION

In accordance with the invention, a trialkyl methanetricarboxylate of the general formula:

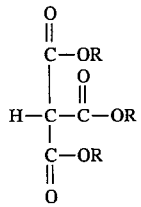

wherein R has the above-mentioned meaning, is converted into the end product (formula I) with a disubstituted ethane of the general formula:

$$X\text{—}CH_2\text{—}CH_2\text{—}X \qquad III$$

wherein the two substituents X are identical or different and have the abovementioned meaning, in the presence of an alkaline earth metal carbonate or alkali metal carbonate.

The trialkyl methanetricarboxylate of the general formula II, which is employed as the starting material, can be prepared in a known manner in accordance with H. Lund & A. Voigt in Organic Syntheses, Collect. Vol. II, Wiley, New York, (1946), p. 594. The disubstituted ethanes which are employed as starting materials, for example, dibromoethane, are commercial products. Examples of the trialkyl methanetricarboxylate (formula II) which is employed are trimethyl, triethyl, tripropyl, triisopropyl, tributyl, triisobutyl, tripentyl, triisopentyl, trihexyl and triisohexyl methanetricarboxylate. It is preferred to employ triethyl methanetricarboxylate. Examples of the disubstituted ethane (formula III) which is employed are 1,2-dibromoethane, 1,2-dichloroethane, 1,2-diiodoethane, 1-bromo-2-chloroethane, 1-bromo-2-iodoethane, 1-iodo-2-chloroethane, 1-bromo-2-mesyloxyethane, 1-chloro-2-mesyloxyethane, 1-iodo-2-mesyloxyethane, 1-bromo-2-tosyloxyethane, 1-chloro-2-tosyloxyethane and 1-iodo-2-tosyloxyethane. It is preferred to use 1,2-dibromoethane.

Examples of the alkaline earth metal carbonate which is employed are magnesium and calcium carbonate. Potassium and sodium carbonate are examples of the alkali metal carbonate. It is preferred to employ an alkali metal carbonate, such as, potassium and sodium carbonate, especially potassium carbonate.

The reaction is expediently carried out in a polar aprotic solvent. Examples of suitable polar aprotic solvents are dimethylformamide, dimethylacetamide and N-methylpyrrolidone. The reaction is preferably carried out in dimethylformamide. The reaction is expediently carried out at a temperature from 0° C. to the reflux temperature of the solvent concerned, prefereably from 20° to 90° C.

After a reaction time of about 0.5 to 5 hours, it is then possible to obtain the end product of formula I by methods of working up which are customary to the person skilled in the art. In comparison with the known process according to H. Rapoport, et al. [J. Org. Chem., Vol. 44, No. 20, (1979), 3492–3496]and in comparison with the process carried out in accordance with Example 2 of the present application, the process according to the invention enables the end products to be obtained in a substantially shorter reaction time, in high purity and with a high yield.

EXAMPLE 1

Preparation of bromo triethyl ester (with $K_2CO_3$)

An initial charge of 100.0 g (0.43 mol) of triethyl methanetricarboxylate, 290 ml of dimethylformamide and 59.5 g (0.43 mol) of $K_2CO_3$ was heated to 60° C. over the course of 15 min. The white suspension was stirred at this temperature for a further 15 min., and then 120 g (0.63 mol) of dibromoethane were added at 60° C. over the course of one hour and 40 min. The mixture was subsequently stirred at 60° C. for 20 min. For working up, the suspension was cooled in an ice bath, and then 500 ml of water were added. The organic phase was extracted with 240 ml of toluene. 200 ml of water was added to the combined organic phases (pH=8.6), and the two-phase mixture was thoroughly mixed and adjusted to a pH of 12.3 using 11.06 g of 10% strength NaOH solution. After stirring for 10 min. the phases were separated. The solvent was distilled off in one pass through a Luwa apparatus (conditions: water pump vacuum, oil temperature 118° C., speed of rotation 1250 rpm, feed rate 4–5 ml/min.). 126.2 g of bromo triethyl ester (purity 94 percent, area percent) was obtained. The conditions for the second pass were: vacuum 5 mbar, oil temperature 197° C., 1250 rpm, feed rate 2–3 ml/min. A total of 116.2 g of bromo triethyl ester was obtained (purity 98.7 percent, area percent), corresponding to a yield of 80 percent based on the triethyl methanetricarboxylate employed.

EXAMPLE 2

Preparation of bromo triethyl ester (with sodium ethanolate; comparative example)

100 g (0.43 mol) of triethyl methanetricarboxylate was dissolved in 290 ml of dimethylformamide, and 30.9 g (0.42 mol) of sodium ethanolate was added. The temperature rose to 60° C. Subsequently 55 ml of dimethylformamide/ethanol mixture was distilled off over 45 min. under a water pump vacuum at a still temperature of 50° C. A further 55 ml of dimethylformamide was added. The reaction mixture was heated to 75° to 80° C., during which 157 g (0.83 mol) of dibromoethane was added over the course of 90 min. The suspension formed was subsequently stirred at 80° C. for 3 h, and worked up as follows. For working up, 240 ml of deionized water and 240 ml of toluene were added at room temperature to the suspension (the temperature rose to 40° C.). Using 18.5 g of 10% strength aqueous NaOH solution, the pH of the two-phase mixture was adjusted from 7 to 12.5; this mixture was stirred for 15 min. and then the phases were separated. The basic aqueous phase was extracted with 120 ml of toluene (about 12 percent of bromo triethyl ester was additionally obtained in this way). The organic phases were combined (crude yield 94.4 percent). Distillation in a thin-film evaporator (water pump vacuum, 110° C. oil temperature, 1250 rpm, 4–5 ml/min.) gave 131 g of crude bromo triethyl ester (purity: 92.5 percent, 1.3 percent of bromo triethyl ester was in the distillate). A second distillation pass in the thin-film evaporator gave 120 g of bromo triethyl ester (purity 94.8 percent), corresponding to a yield of 82 percent based on triethyl methanetricarboxylate. In contrast to Example 1, this method gave bromo triethyl ester in a poorer quality, since this ester was more contaminated by at least 4 percent.

What is claimed is:

1. A process for the preparation of a trialkyl ester derivative of the general formula:

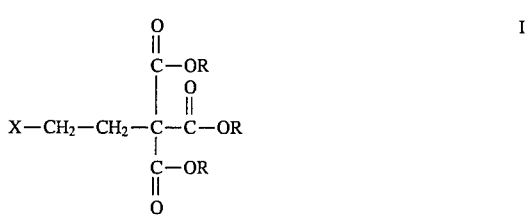

wherein X is chlorine, bromine, iodine, tosyloxy- or mesyloxy- and R is a $C_1$-$C_6$-alkyl group, comprising a trialkyl methanetricarboxylate of the general formula:

wherein R has the meaning given above, is convened into the trialkyl ester derivative formula I with a disubstituted ethane of formula:

wherein the two substituents X are identical or different and have the meaning given above, in the presence of an alkaline earth metal carbonate or an alkali metal carbonate.

2. The process according to claim 1, wherein the reaction is carried out in a polar aprotic solvent.

3. The process according to claim 2 wherein dimethylformamide is employed as the polar aprotic solvent.

4. The process according to claim 3 wherein the reaction is carried out in the presence of an alkali metal carbonate.

5. The process according to claim 4 wherein the alkali metal carbonate employed is potassium carbonate or sodium carbonate.

6. The process according to claim 5 wherein 1,2-dibromoethane is the disubstituted ethane.

7. The process according to claim 6 wherein the trialkyl methanetricarboxylate is triethyl methanetricarboxylate.

8. The process according to claim 7 wherein the reaction is carried out at a temperature from 0° C. to the reflux temperature of the polar aprotic solvent used in the reaction.

9. The process according to claim 1 wherein the reaction is carried out in the presence of an alkali metal carbonate.

10. The process according to claim 9 wherein the alkali metal carbonate is potassium carbonate or sodium carbonate.

11. The process according to claim 1 wherein 1,2-dibromoethane is employed as the disubstituted ethane.

12. The process according to claim 1 wherein the trialkyl methanetricarboxylate is triethyl methanetricarboxylate.

13. The process according to claim 1 wherein the reaction is carried out in a polar aprotic solvent and at a temperature from 0° C. to the reflux temperature of the polar solvent.

* * * * *